(12) United States Patent
Hwang et al.

(10) Patent No.: US 11,890,075 B2
(45) Date of Patent: Feb. 6, 2024

(54) PORTABLE COMPLEX SENSOR DEVICE FOR MEASURING MULTIPLE ITEMS OF BIOMETRIC INFORMATION, AND MEASUREMENT METHOD

(71) Applicant: HEXACHECK INC., Daejeon (KR)

(72) Inventors: In Deok Hwang, Sejong (KR); Chang Hwan Kim, Daejeon (KR)

(73) Assignee: HEXACHECK INC., Daejeon (KR)

( * ) Notice: Subject to any disclaimer, the term of this patent is extended or adjusted under 35 U.S.C. 154(b) by 708 days.

(21) Appl. No.: 17/097,239

(22) Filed: Nov. 13, 2020

(65) Prior Publication Data

US 2021/0059525 A1 Mar. 4, 2021

Related U.S. Application Data

(63) Continuation-in-part of application No. 16/063,963, filed as application No. PCT/KR2017/008579 on Aug. 8, 2017, now Pat. No. 10,849,541.

(30) Foreign Application Priority Data

Aug. 8, 2016 (KR) .................. 10-2016-0100635

(51) Int. Cl.
*A61B 5/00* (2006.01)
*A61B 5/145* (2006.01)
*H04W 4/80* (2018.01)
*A61B 5/15* (2006.01)
*H04W 4/38* (2018.01)
*A61B 5/25* (2021.01)
*A61B 5/332* (2021.01)

(52) U.S. Cl.
CPC ........ *A61B 5/0006* (2013.01); *A61B 5/14532* (2013.01); *A61B 5/150358* (2013.01); *A61B 5/25* (2021.01); *A61B 5/332* (2021.01); *H04W 4/38* (2018.02); *H04W 4/80* (2018.02)

(58) Field of Classification Search
CPC .............. A61B 5/0006; A61B 5/14532; A61B 5/150358; A61B 5/25; A61B 5/332
See application file for complete search history.

(56) References Cited

U.S. PATENT DOCUMENTS

| | | | | |
|---|---|---|---|---|
| 2012/0255875 | A1* | 10/2012 | Vicente | A61B 5/0004 600/347 |
| 2014/0073979 | A1* | 3/2014 | Inciardi | G16Z 99/00 600/509 |
| 2014/0200469 | A1* | 7/2014 | Bocko | A61B 5/346 600/509 |

* cited by examiner

*Primary Examiner* — Amanda K Hulbert
*Assistant Examiner* — Philip C Edwards
(74) *Attorney, Agent, or Firm* — Osha Bergman Watanabe & Burton LLP

(57) ABSTRACT

A portable complex sensor device for measuring multiple items of biometric information, according to the present invention, comprises: a plurality of electrodes for receiving the biometric information; a plurality of biometric information measuring circuits for measuring the biometric information received from the plurality of electrodes; a plurality of current sensors which are always supplied with power so as to sense electric current when an object to be measured contacts the electrodes; a wireless communication means for transmitting and receiving data to and from a smart phone; and a microcontroller for controlling the power supply of a battery by being operated in a sleep mode or an active mode on the basis of whether the current sensors have sensed the electric current.

11 Claims, 7 Drawing Sheets

PORTABLE COMPLEX SENSOR DEVICE FOR MEASURING MULTIPLE ITEMS OF BIOMETRIC INFORMATION, AND MEASUREMENT METHOD

CROSS REFERENCE TO RELATED APPLICATIONS

This application is a continuation-in-part application of U.S. patent application Ser. No. 16/063,963, filed on Jun. 19, 2018, which is the U.S. national stage application of PCT Application No. PCT/KR2017/008579, filed on Aug. 8, 2017, which claims priority to Korean Patent Application No. 10-2016-0100635, filed on Aug. 8, 2016. The entire contents of these applications are incorporated herein by reference.

TECHNICAL FIELD

The present invention relates to a portable complex sensor device for measuring a plurality of pieces of biometric information and a measurement method, and more particularly, to a card-type portable complex sensor device that is, as a single complex sensor device, capable of automatically selecting and measuring different types of test items including an electrocardiogram and blood glucose and displaying measurement results on a smartphone and a measurement method therefor by wirelessly connecting the portable complex sensor device to the smartphone.

BACKGROUND ART

As portable health measurement devices, products for measuring a single item such as blood glucose or an electrocardiogram (ECG) are commercially available, but for the measurement of a plurality of test items including blood glucose and an electrocardiogram, there has been inconvenience for a user to separately carry respective measurement devices. Thus, complex sensor measurement devices capable of measuring different types of measurement items in a single device are needed. These complex sensor measurement devices should be small-sized with a small volume, and power consumption thereof should be low for long-term use of a battery.

As a prior art, Korean Patent Publication No. 10-2014-0065801 discloses a sensor input system and a technique in which a sensor is selected according to a selection signal selected from a portable terminal.

Generally, a single portable complex sensor measurement device requires a power switch, a selection switch for choosing a test item, and a display configured to show measured data. However, such a mechanical power switch or a mechanical selection switch and a display increase the volume or area of the portable measurement device and cause battery power consumption problem and a limitation on miniaturization. In addition, unless a blood glucose measurement circuit and an ECG measurement circuit of a complex sensor device are separately configured and power supply thereto is separately controlled, all the circuits operate when power is turned on and thus power consumption increases, and therefore, it is necessary to operate only a circuit of the required function.

DISCLOSURE

Technical Problem

The present invention has been made in view of the above problems and needs, and an object of the present invention is to provide a portable complex sensor device that performs operations by automatically selecting only the corresponding measurement circuit in a single complex sensor device without using a mechanical switch so that miniaturization is achieved, and displays measurement results on a smartphone.

Technical Solution

According to one aspect of the present invention, provided is a portable complex sensor device for measuring a plurality of pieces of biometric information, including: a plurality of biometric information measurement circuit units configured to measure the plurality of pieces of biometric information; a plurality of input terminal sets allowing each of the plurality of biometric information measurement circuit units to receive an input signal; a plurality of current sensors configured such that, when a subject having biometric information is electrically connected to one of the plurality of input terminal sets, a current flows in the subject having biometric information through the electrically connected input terminal set, configured to generate an output signal when sensing the current, and supplied with power at all times; an AD converter connected to an output terminal of each of the biometric information measurement circuit units and configured to convert an analog signal into a digital signal; a wireless communication device configured to transmit or receive data to or from a smartphone; and a microcontroller configured to receive an output of the AD converter, wherein the microcontroller is supplied with power of a battery embedded in the portable complex sensor device; when the portable complex sensor device is not in use for biometric information measurement, the microcontroller operates in a sleep mode and the plurality of biometric information measurement circuit units, the AD converter, and the wireless communication device are powered off; the microcontroller operates in an active mode when receiving the output signal of the current sensor, and controls one of the plurality of biometric information measurement circuit units corresponding to the current sensor, the AD converter, and the wireless communication device to be powered on; the portable complex sensor device displays measured biometric information data on a screen of the smartphone; and the portable complex sensor device is a thin credit card type, and includes a plurality of electrocardiogram electrodes and a blood test strip insertion hole at a case of the portable complex sensor device.

The plurality of pieces of biometric information includes electrocardiogram information and blood information, and the blood information includes at least one of a blood glucose level, a ketone level, and an international normalized ratio (INR).

The wireless communication device supports Bluetooth low energy (BLE).

The current sensed by the current sensor is a direct current.

According to another aspect of the present invention, provided is a method of measuring a plurality of pieces of biometric information by using a portable complex sensor device and a smartphone, including: displaying a plurality of selection buttons used to select biometric information, on a display of the smartphone when a smartphone application is executed; when one of the plurality of selection buttons is selected and contacted, transmitting information of the corresponding button to the portable complex sensor device; activating a microcontroller of the portable complex sensor device using one of a plurality of current sensors; receiving the information of the corresponding button through a wireless communication device, the receiving being performed by the activated microcontroller; powering on a biometric information measurement circuit unit corresponding to the received button information and performing a measurement operation, the powering and the performing being performed by the microcontroller; powering on an AD converter, performing AD conversion of an output of the biometric information measurement circuit unit, and transmitting the output to the microcontroller, the powering being performed by the microcontroller and the performing and transmitting being performed by the AD converter; transmitting the measured biometric information to the smartphone via the wireless communication device, the transmitting being performed by the microcontroller; displaying the measured biometric information on a screen of the smartphone; and storing the measured biometric information in a memory of the smartphone.

Advantageous Effects

A portable complex sensor device according to the present invention, which is a single credit card-type device, is convenient to carry and thus is not limited by time and place, can measure a plurality of pieces of medical information, and wirelessly communicates with a smartphone, thus provides user convenience.

In addition, when the portable complex sensor device according to the present invention is not in use, all circuits except for current sensors are powered off and only a microcontroller enters into a sleep mode, whereas when in use, the microcontroller enters into an active mode and power is delivered to only a target circuit. Accordingly, power consumption of a battery embedded in the portable complex sensor device can be maximally reduced.

In addition, the portable complex sensor device according to the present invention does not include a mechanical power switch or a mechanical selection switch, and thus can be miniaturized and thinned and does not cause unnecessary inconvenience due to the use of switches by a user, the possibility of switch malfunction, a limited lifespan, and an increase in manufacturing costs. In addition, when a user uses the portable complex sensor device, a user does not need to know which switch should be used when or how, and thus it is convenient to use.

In addition, the portable complex sensor device according to the present invention does not include a display such as a LCD or the like, thus not causing the possibility of display breakdown, deterioration of a display, and an increase in manufacturing costs, and is small in size and thus it is convenient to use.

BEST MODE

Figure 1:
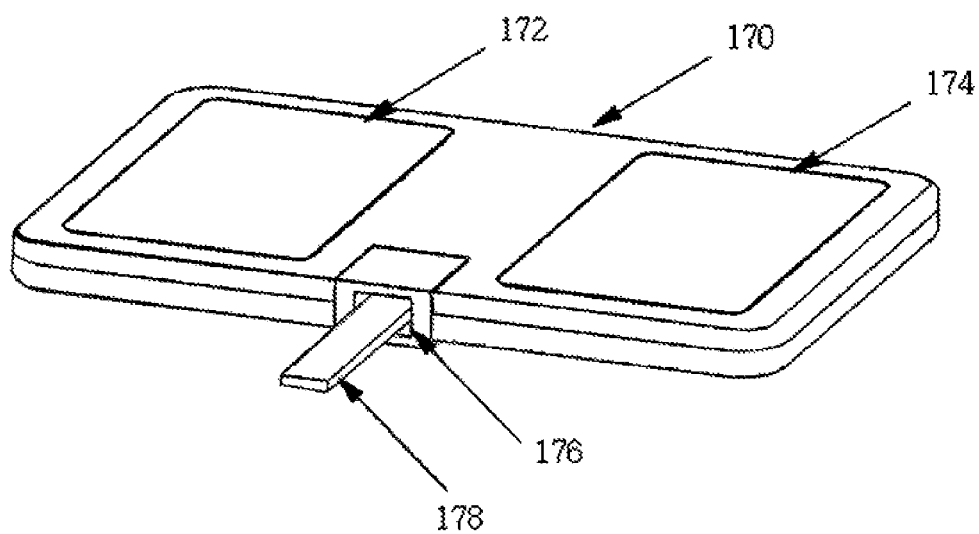
FIG. 1 is a perspective view of a portable complex sensor device according to the present invention.

Hereinafter, embodiments of the present invention will be described with reference to the accompanying drawings. In the present embodiment, a case in which a portable complex sensor device includes an electrocardiogram (ECG) measurement device and a blood glucose measurement device in a combined form will be described as an example, but the present invention is not limited thereto. The blood glucose measurement device may be a device with a function of measuring blood information other than blood glucose, for example, a ketone level or an international normalized ratio (INR) of a drop of capillary blood on a blood test strip.

The electrocardiogram measurement is performed by bringing two or more electrodes into contact with different sites of a human body and measuring one or more voltages generated from the heart. When an electrocardiogram is measured by bringing the more electrodes into contact with predetermined specific sites of a human body, the more pieces of information on the activity of the heart can be acquired. Thus, although the embodiments of the present invention, which will be described below, describe the portable complex sensor device when it has a pair of electrocardiogram electrodes, the portable complex sensor device according to the present invention may include more than a pair of electrocardiogram electrodes in other cases of the portable complex sensor device according to the present invention.

The blood glucose level or the ketone level may be measured using an amperometric method. The INR is a measure of blood coagulation tendency and may be measured using an electrical impedance method, an amperometric method, a mechanical method, or the like, for capillary blood. A blood test strip insertion hole that enables a blood test strip needed for the blood characteristic test to be inserted therethrough may be included at a case of the portable complex sensor device according to the present invention.

The portable complex sensor device for measuring an ECG and a blood glucose level has been made to address the following problems and drawbacks.

The first problem is as follows. For the maximization of user convenience, there should be no need for a user to keep or carefully read the manual. In addition, as simple a user manual as possible is preferable. In addition, it is required that a user use a device using only as few rules as possible. It is more preferable that a user can use a device without usage rules. In a case in which a user uses a measurement system without usage rules, the measurement system should cope with an arbitrary method used by a user. For example, a user may first execute a smartphone application, or may first operate a current sensor of the complex sensor device. Thus, the smartphone application and the complex sensor device should provide desired results regardless of an operation order of a user. Therefore, it is necessary to configure the smartphone application and the electronic circuits and the firmware of the complex sensor device to provide desired results without errors for a number of cases of all possible operation orders. However, it is difficult to configure the smartphone application and the electronic circuits and the firmware of the complex sensor device to cope with any usage method not in accordance with automatic operation orders without usage rules.

The second problem is as follows. When a blood glucose level is measured using a complex sensor device capable of measuring an ECG and a blood glucose level, a user may unconsciously touch an ECG electrode attached to the complex sensor device. In this case, a current sensor corresponding to ECG measurement operates, and this causes the complex sensor device to start measuring an undesired ECG, and then undesired ECG measurement results will be displayed on a smartphone display. Thus, when measuring a blood glucose level, ECG measurement should not start even though a user unconsciously touches ECG electrodes. However, this is not in accordance with an originally planned operation method in which an ECG measurement starts when ECG electrodes are touched for an ECG measurement.

The third problem is as follows. It is possible that a user use an operation method including the following processes 1), 2), and 3): 1) For ECG measurement, first, a user who intends to operate a complex sensor device touches a pair of electrodes of the complex sensor device. At this time, a current sensor operates and consequently, the complex sensor device is powered on; 2) Then the user executes a smartphone application for the ECG measurement and selects ECG measurement; and 3) For the ECG measurement, the user starts ECG measurement by touching again the pair of electrodes of the complex sensor device. However, the method including the processes 1), 2), and 3) described above causes the following drawbacks. As soon as the pair of electrodes of the complex sensor device is first touched, the complex sensor device becomes powered on immediately, and thus the second touch becomes a meaningless action. To solve this problem, there arises a difficulty in distinguishing the first touch from the second touch and the distinguished touches should be treated separately. This problem may be easily solved when there are usage rules and a user uses the complex sensor device according to the usage rules. However, it is rather preferable to allow the user to use the above sequence and make solutions capable of accommodating it.

The fourth problem is as follows. In the case of ECG measurement, it is required that ECG measurement is generally performed for a certain period of time, for example, 30 seconds. For this, an ECG may be measured for 30 seconds from when a pair of electrodes of a complex sensor device are touched and connected to a smartphone. However, this can be possible only when a measurement start point can be determined. In the sequence including the processes 1), 2), and 3) described in the above third problem, it is difficult to determine when the measurement start point is.

The fifth problem is as follows. When a blood glucose level is measured using a complex sensor device, it takes a considerable period of time to insert a blood test strip into a strip insertion hole of the complex sensor device, put blood on the strip, and complete measurement. During this period of time, it is necessary to block communication between the complex sensor device and a smartphone to reduce battery consumption. Thus, it is preferable that the complex sensor device transmits measurement results to a smartphone only after blood glucose level measurement is completed. In addition, since it is clear that a user wants to measure a blood glucose level when a blood test strip is inserted into a strip insertion hole, the user does not need to select a blood glucose measurement button in a smartphone display and needs only to start a smartphone application. However, in other cases, another user who wants to measure blood glucose may first try to select a blood glucose measurement button in a smartphone display. Thus, the smartphone application should accept the above two usage methods by various users who want to measure blood glucose.

The sixth problem is as follows. It is necessary to power on only an ECG measurement circuit for ECG measurement, and it is necessary to power on only a blood glucose measurement circuit for blood glucose measurement. Otherwise, battery power is wasted. However, there is a need to solve this problem without using a power switch or selection switch for each circuit.

The seventh problem is as follows. For ECG measurement, analog-to-digital (AD) conversion should be performed on an output of an ECG measurement circuit, and for blood glucose measurement, AD conversion should be performed on an output of a blood glucose measurement circuit. That is, when a single AD converter is used, an input of the AD converter should be selected to an output of a target measurement circuit. However, this problem should be solved in a state in which there is no selection switch in the complex sensor device.

The present invention solves the above-described problems through systematic circuit design and software design.

FIG. 1 is a perspective view of a portable complex sensor device according to the present invention. The portable complex sensor device 170 includes a pair of electrodes 172 and 174 configured to measure an ECG and spaced apart from each other on an upper surface thereof by a predetermined distance, and a blood test strip insertion hole 176 formed in a side surface thereof and allowing a blood test strip 178 to be inserted thereinto for blood glucose measurement.

The portable complex sensor device according to the present invention may be a credit card type with a thickness of less than 6 mm for high portability. A power supply may be a CR2032-type battery considering desirable lifespan of about two years.

In addition, the portable complex sensor device does not include a mechanical power switch or a mechanical selection switch for miniaturization thereof, and does not use a display to reduce power consumption.

For the portable complex sensor device according to the present invention, current sensors are used instead of using a mechanical power switch or a mechanical selection switch. The current sensors are supplied with power needed for operation at all times and stand by to generate an output signal when an event occurs. When a subject having biometric information is electrically connected with one of the current sensors, a loop through which a current can flow is formed. Thus, when the subject having biometric information is electrically connected to the current sensor, the current sensor allows a minute current to flow in the subject having biometric information, and the current sensor senses the minute current and generates an output signal. When the portable complex sensor device is not in use, only the current sensors operate and the remaining circuits are powered off, while a microcontroller waits in a sleep mode. When a current sensor senses a current through the insertion of a blood test strip or the occurrence of an event in which electrodes are touched by both hands, the microcontroller is activated and turns the corresponding circuits on.

The current sensed by the current sensors are supplied from a battery included in the portable complex sensor device and may be a direct current.

Figure 2:
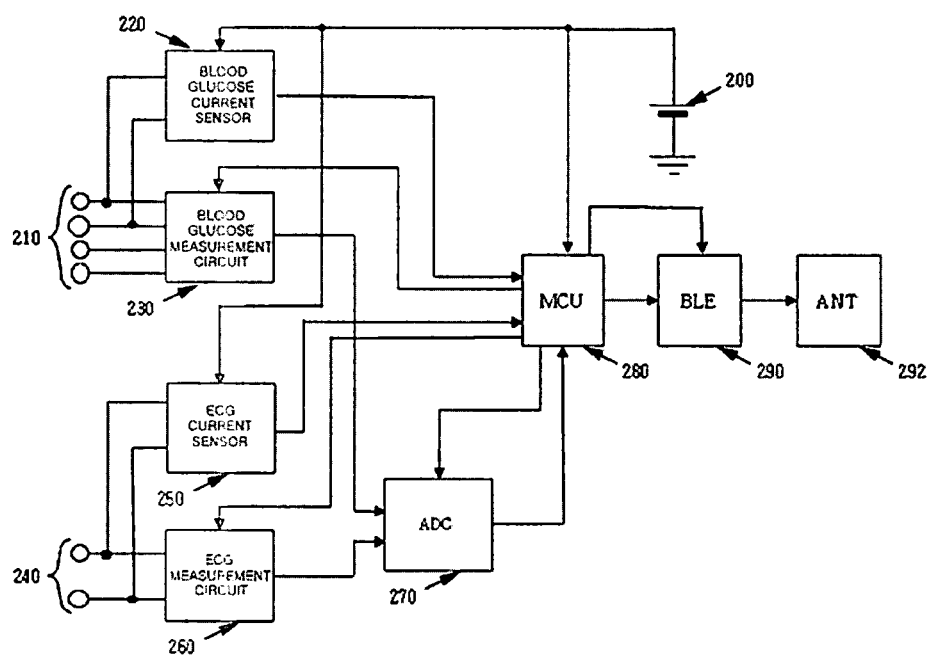
FIG. 2 is a block diagram of a circuit embedded in a portable complex sensor device according to an embodiment of the present invention.
Figure 3:
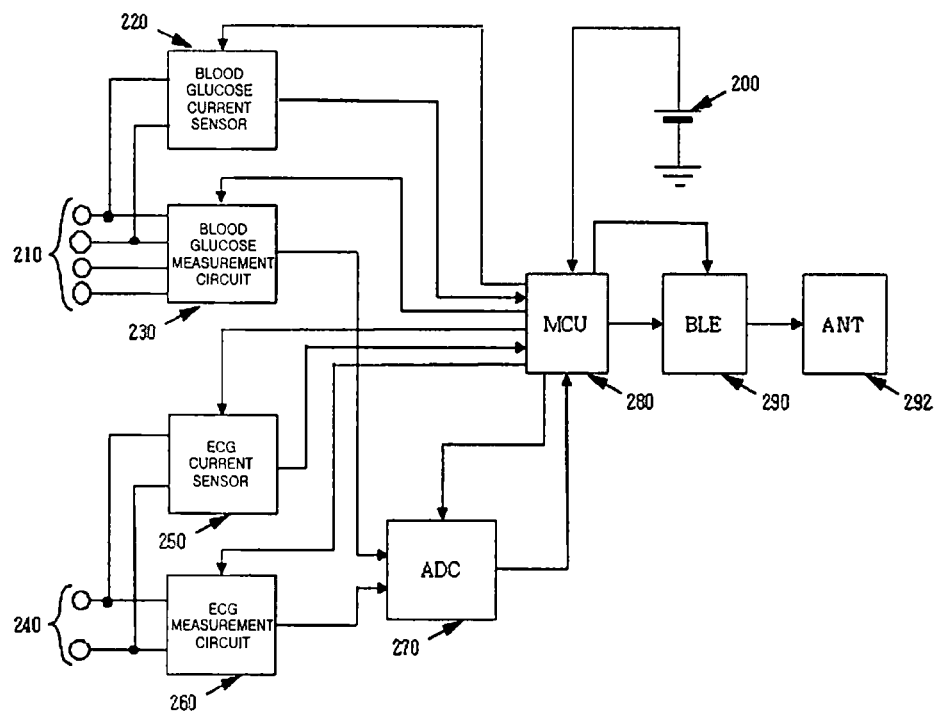
FIG. 3 is a block diagram of a circuit embedded in a portable complex sensor device according to another embodiment of the present invention.

FIGS. 2 and 3 are example block diagrams respectively illustrating a circuit embedded in the portable complex sensor device according to the present invention. Each block illustrated in FIGS. 2 and 3 may be realized using commercialized components by a conventional technique.

FIG. 2 illustrates an embodiment of a portable complex sensor device 170 in which both a microcontroller 280 and a plurality of current sensors 220 and 250 are directly connected to a battery 200 so that power is supplied thereto and a power switch is not included. All arrows illustrated as entering the top of each block denote power supply lines. Except for an arrow coming out from a microcontroller 280 and entering an input terminal of a wireless communication device 290, arrows illustrated as coming out of a battery 200 and the microcontroller 280 denote power supply lines. Power of a blood glucose current sensor 220 and an ECG current sensor 250 is directly supplied from the battery 200 via the power supply lines directly connected to the battery 200. When the microcontroller 280 sets power supply lines coming out from the microcontroller 280 High, a blood glucose measurement circuit unit 230, an ECG measurement circuit unit 260, an AD converter 270, and the wireless communication device 290 may be supplied with power, and when the microcontroller 280 sets the power supply lines coming out from the microcontroller 280 Low, the above-described elements are powered off. Herein, High and Low denote voltages, and for example, High is 3 V and Low is 0 V.

FIG. 3 illustrates a second embodiment in which only the microcontroller 280 is directly connected to the battery 200 so that power is supplied thereto from the battery 200 and a power switch is not included. When the microcontroller 280 sets power supply lines High, a plurality of current sensors 220 and 250, a plurality of biometric information measurement circuit units 230 and 260, the AD converter 270, and the wireless communication device 290 may be supplied with power, and when the microcontroller 280 sets the power supply lines Low, the above-described components are powered off. Even when the microcontroller 280 is in a sleep mode, power is supplied to the blood glucose current sensor 220 and the ECG current sensor 250 via the power supply line of the microcontroller 280.

In FIGS. 2 and 3, an input terminal set 210 is arranged in a blood test strip insertion hole 176 and indicates a plurality of electrical terminals configured to electrically connect a blood test strip 178 to the input terminal of the blood glucose measurement circuit unit 230 when the blood test strip 178 is inserted into the blood test strip insertion hole 176. In addition, in FIGS. 2 and 3, an input terminal set 240 indicates a plurality of electrical terminals configured to electrically connect a plurality of ECG electrodes arranged at a case of the portable complex sensor device according to the present invention to the input terminals of the ECG measurement circuit unit 230.

Although FIGS. 2 and 3 illustrate that the current sensor 250 and the microcontroller 280 are supplied with power from the battery 200, the current sensor 250 and the microcontroller 280 may be supplied with power via a DC-DC converter or a voltage regulator supplied with power from the battery 200. In addition, although FIGS. 2 and 3 illustrate that the biometric information measurement circuit units 230 and 260, the AD converter 270, and the wireless communication device 290 are powered ON/OFF by the microcontroller, in some embodiments, the biometric information measurement circuit units 230 and 260, the AD converter 270, and the wireless communication device 290 may be supplied with power via a DC-DC converter or a voltage regulator, and the DC-DC converter or the voltage regulator may be powered ON/OFF by the microcontroller 280. In addition, arrows illustrated as coming out of the microcontroller 280 may denote lines for controlling power supply of the corresponding blocks.

Blood glucose measurement according to the present invention is performed as follows. When a user inserts the blood test strip 178 into the blood test strip insertion hole 176, the input terminal set 210 is electrically connected to the blood test strip 178. At this time, the blood glucose current sensor 220 senses a minute current flowing through the blood test strip 178 and automatically generates an output signal. The output signal of the blood glucose current sensor 220 activates the microcontroller 280 having been in a sleep mode. As a result, the microcontroller 280 powers on the blood glucose measurement circuit unit 230 and the AD converter 270. The blood glucose measurement circuit unit 230 performs blood glucose measurement when blood is put on the blood test strip 178 and generates an output signal. The output signal of the blood glucose measurement circuit unit 230 is converted into a digital signal by the AD converter 270. The digital signal is converted to a blood glucose level by the microcontroller 280 and the obtained blood glucose level is transmitted to a smartphone via the wireless communication device 290 and an antenna 292. The smartphone displays the blood glucose level on a screen of the smartphone.

The ECG measurement according to the present invention is performed as follows. When a user touches the pair of electrodes 172 and 174 with both hands, the ECG current sensor 250 allows a minute current to flow through the both hands and detects the minute current flowing through the both hands. Then, the current sensor 250 changes the microcontroller 280 from a sleep mode to an active mode. Consequently, the microcontroller 280 powers on the ECG measurement circuit unit 260 and the AD converter 270 and transmits an output of the AD converter 270 receiving an output of the ECG measurement circuit unit 260 to a smartphone via the wireless communication device 290. The smartphone receiving the data displays an ECG waveform. When measurement for a certain period of time is completed, the microcontroller 280 enters into a sleep mode and waits for the next touch of both hands.

Figure 4:
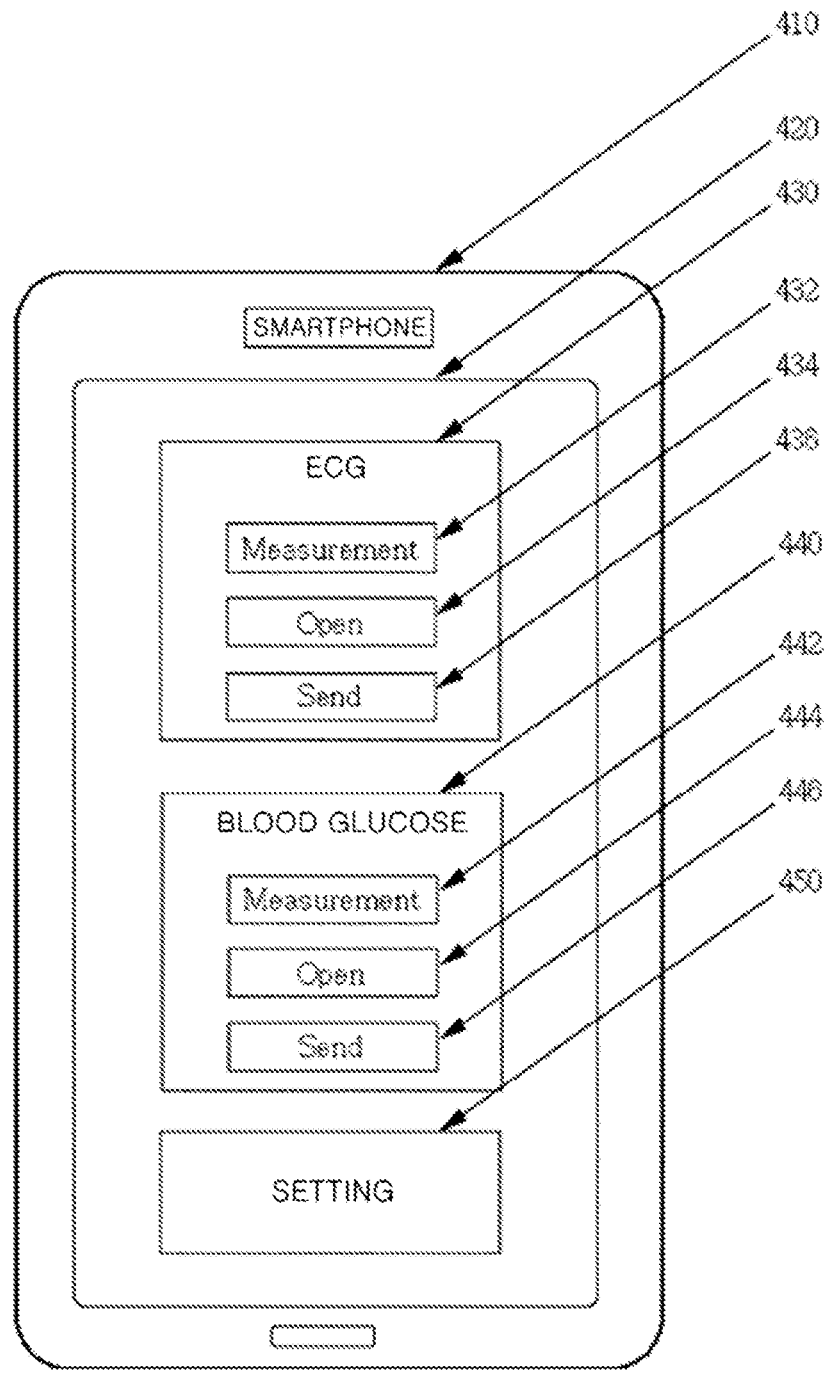
FIG. 4 is an exemplary diagram of a smartphone display when a smartphone application according to the present invention is executed.

FIG. 4 is an exemplary view illustrating a case in which a smartphone application according to the present invention is executed, and illustrates touch buttons 432, 434, 436, 442, 444, 446, and 450 on a display 420 of a smartphone 410. To measure an ECG, a user touches the ECG measurement button 432. Subsequently, when the pair of electrodes 172 and 174 of the complex sensor device 170 are respectively touched with both hands of a user, as described above, an ECG is measured in the complex sensor device 170 and the measured ECG is displayed in a chart form on the display 420, and the measured data is stored in the smartphone 410. When a user wants to see the previously stored ECG measurement data again in a chart form, the user touches the open button 434. To transmit the stored data to a doctor or a hospital, the send button 436 is touched.

For blood glucose level measurement, a user touches the blood glucose measurement button 442. When the user inserts the blood test strip 178 into the blood test strip insertion hole 176 and puts blood on the blood test strip 178, as described above, blood glucose measurement is performed in the complex sensor device 170 and measurement results are displayed on the display 420 of the smartphone 410. When the user wants to see the previously stored blood glucose level again in a chart form, the open button 444 is touched. To transmit the stored data to a doctor or a hospital, the send button 446 is touched.

The buttons 432, 434, and 436 related to an ECG are configured in an ECG box 430, and the buttons 442, 444, and 446 related to blood glucose are configured in a blood glucose box 440. The setting button 450 is touched when intending to record a name, birth date, gender, an address, and the like of a user or to set selection items.

Figure 5:
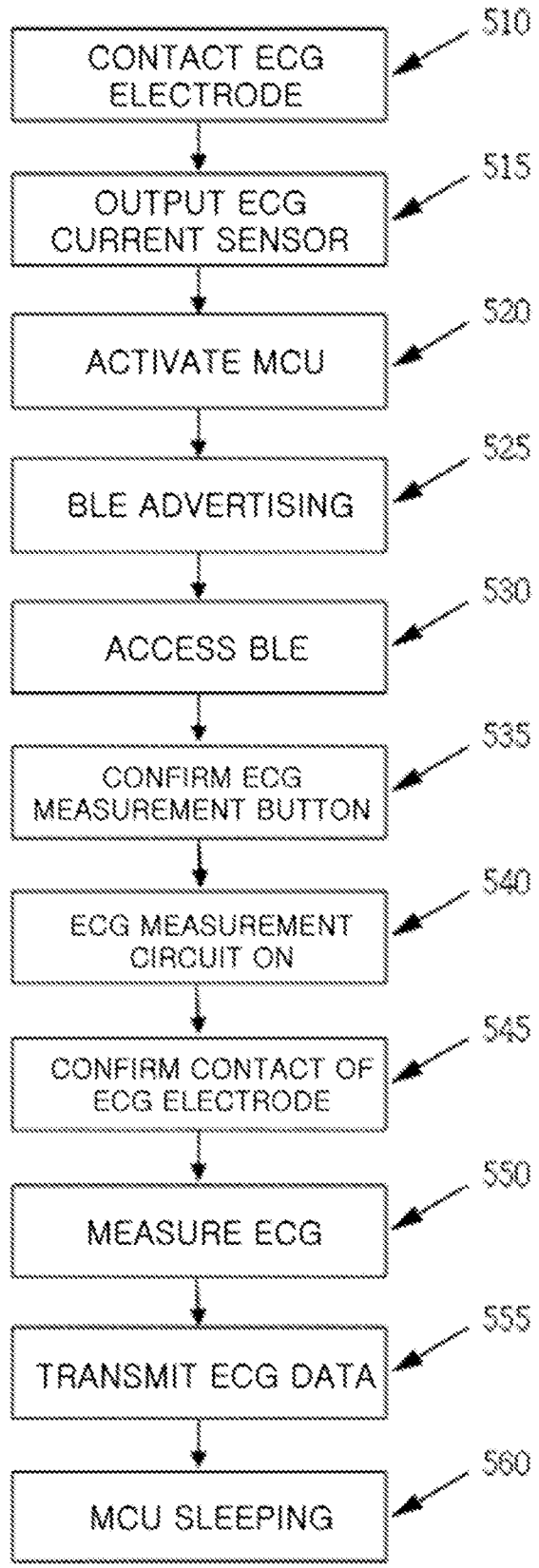
FIG. 5 is an operation flowchart of a complex sensor device according to the present invention when an electrocardiogram is measured.

FIG. 5 is an operation flowchart of the complex sensor device 170 according to the present invention when an ECG is measured. For ECG measurement, a user touches the pair of electrodes 172 and 174 of the complex sensor device 170 respectively with both hands (operation 510). Then, the current sensor 250 that senses a minute current flowing through a human body between the both hands generates an output signal (operation 515). The output signal causes the microcontroller 280 to be interrupted to thereby activate the microcontroller 280 (operation 520). The activated microcontroller 280 activates the wireless communication device 290. Hereinafter, a case in which the wireless communication device 290 is a Bluetooth low energy device will be described. The wireless communication device 290 of the complex sensor device 170 perform an advertising operation as a Bluetooth low energy peripheral device (operation 525). At this time, the smartphone 410, which has been performing scanning as a Bluetooth low energy central device, discovers and tries to access the complex sensor device 170. At this time, when the complex sensor device 170 approves the access, the smartphone 410 and the complex sensor device 170 are in a Bluetooth low energy connection state (operation 530).

In this regard, when the ECG measurement button 432 of the smartphone 410 is touched (operation 535), the microcontroller 280 powers on the ECG measurement circuit unit 260. As described in the above second problem, the pair of electrodes 172 and 174 of the complex sensor device 170 may be touched unconsciously or in error while a user measures a blood glucose level. Thus, there is a need for a method of distinguishing between whether the pair of electrodes 172 and 174 are touched by a user for ECG measurement and whether to be touched in error. Therefore, in the present invention, the ECG measurement button confirmation process (operation 535) of FIG. 5 is used as a method of distinguishing between reasons why the pair of electrodes 172 and 174 are touched.

The microcontroller 280 that has received a request for ECG measurement selects only the ECG measurement circuit unit 260 to power on (operation 540). Thus, in the present invention, the ECG measurement circuit unit 260 is powered on after confirming that a user intends to request ECG measurement. In addition, as illustrated in FIGS. 2 and 3, this operation is performed by setting an output pin of the microcontroller 280 connected to the ECG measurement circuit unit 260 High. Through this process, the sixth problem is solved.

Next, it is confirmed using the current sensor 250 whether the pair of electrodes 172 and 174 are touched with both hands (operation 545). This process determines when the microcontroller 280 starts ECG measurement, i.e., when to start AD conversion. That is, the fourth problem is solved. When this condition is satisfied, the microcontroller 280 starts ECG measurement (AD conversion) (operation 550). When a user who wants to measure an ECG opens a smartphone application, touches the ECG measurement button 432, and continuously maintains a state in which the pair of electrodes 172 and 174 are touched with both hands, the electrode touch confirmation process (operation 545) is automatically satisfied. Thus, operation 545 does not restrict user convenience or add a limitation to ECG measurement. However, if a user has not yet touched the pair of electrodes 172 and 174 after coming into contact with the pair of electrodes 172 and 174 (operation 510) and touching the ECG measurement button 432 of the smartphone 410, the complex sensor device 170 waits until a user touches the pair of electrodes 172 and 174 again. Therefore, operation 545 of FIG. 5 is one of the important processes of the present invention.

Figure 7:
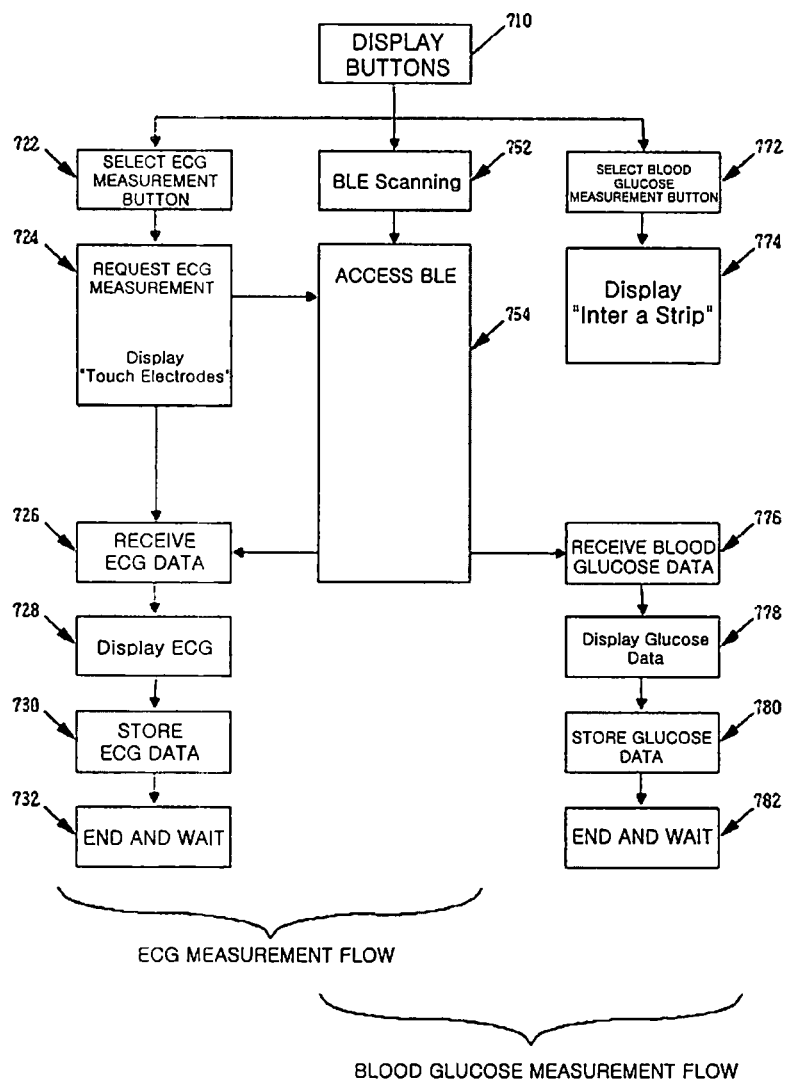
FIG. 7 is a flowchart of a smartphone application according to the present invention.

The above-described third problem is solved by procedures of operation 510 to operation 545 and procedures of an application of FIG. 7 corresponding thereto. That is, the reason why the ECG electrodes 172 and 174 are touched (operation 510) is confirmed by checking whether the ECG measurement button 432 is selected in a smartphone (operation 535), and it is confirmed whether the pair of electrodes 172 and 174 are in a touched state (operation 545), (with the above two confirmations it is confirmed whether the whole preparation for ECG measurement is completed) and thereafter, the ECG measurement starts (operation 550). Accordingly, the third problem is solved. In addition, these processes and procedures provide an accurate start point of ECG measurement (AD conversion) and accordingly, the present invention has solved the fourth problem.

Meanwhile, procedures from operation 510 to operation 545 do not provide inconveniences for a user or do not delay measurement time. After executing an application and then touching the ECG measurement button 432 once in the display 420 of the smartphone 410, a user simply touches the ECG electrodes 172 and 174 to measure an ECG.

After the above process, the microcontroller 280 starts ECG measurement (operation 550). That is, between an input terminal of the AD converter 270, connected to an output of the ECG measurement circuit unit 260 and an input terminal of the AD converter 270, connected to an output of the blood glucose measurement circuit unit 230, the microcontroller 280 sets the AD converter 270 so as to select the former. This operation is performed by setting a configuration register of the microcontroller 280 related to AD conversion. Subsequently, the microcontroller 280 performs AD conversion in accordance with a predetermined AD conversion period and obtains AD conversion results. In the present invention, the seventh problem corresponding to ECG measurement is solved by this process, firmware for executing this process, and the circuit of FIG. 2 or FIG. 3.

The measured ECG data is transmitted to the smartphone 410 (operation 555), and when a predetermined measurement time, for example, 30 seconds has elapsed, the microcontroller 280 enters into a sleep mode (operation 560).

Figure 6:
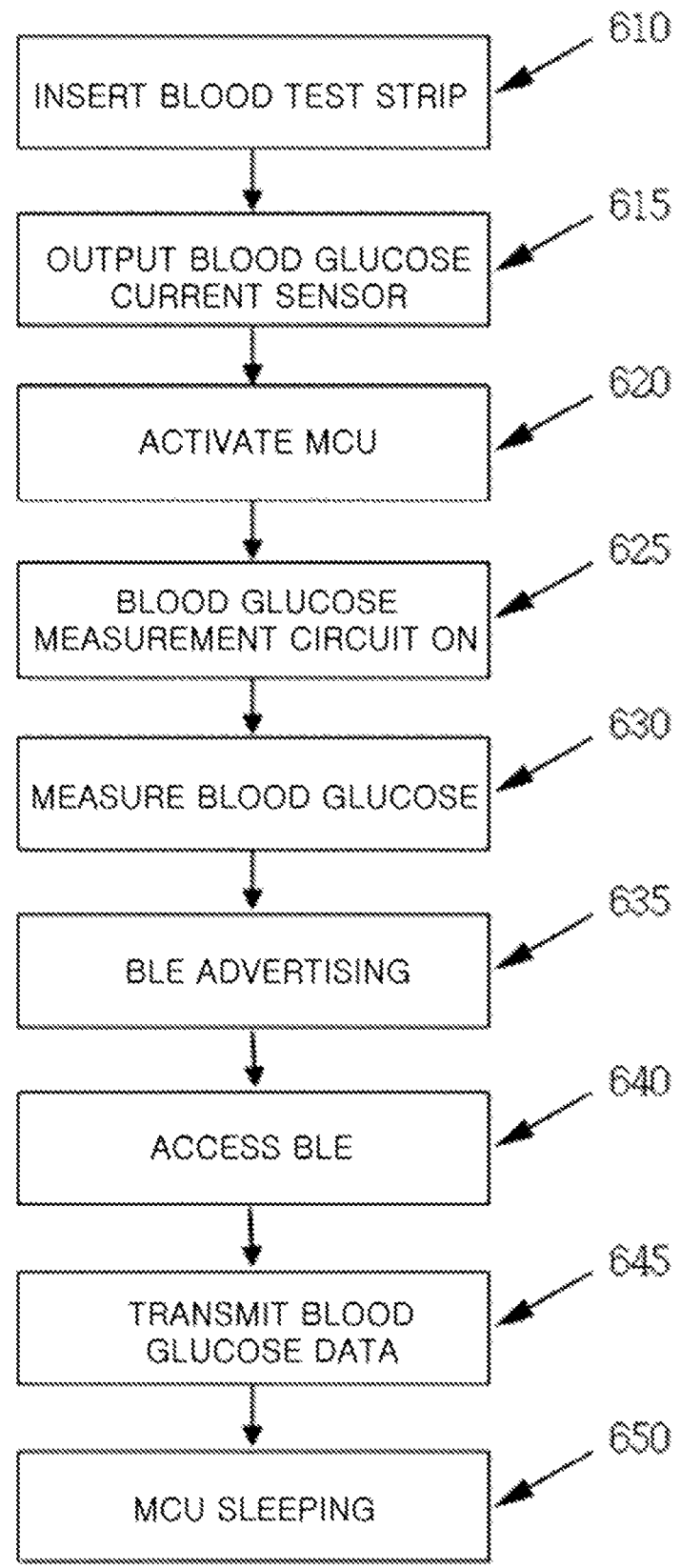
FIG. 6 is an operation flowchart of a complex sensor device according to the present invention when a blood glucose level is measured.

FIG. 6 is an operation flowchart of the complex sensor device 170 according to the present invention when a blood glucose level is measured. To measure a blood glucose level, when a user inserts the blood test strip 178 into the blood test strip insertion hole 176, the blood glucose current sensor 220 detects a minute current and generates an output signal (operation 615). The output signal causes the microcontroller 280 to be interrupted, thereby activating the microcontroller 280 (operation 620). At this time, the microcontroller 280 might have been already activated by an unconscious or erroneous touch of the pair of electrodes 172 and 174, which is the above-described second problem, and thus might have been in an ECG measurement process. However, this problem can be solved by prioritizing an interruption due to the output of the blood glucose current sensor 220 over an interruption due to the output of the ECG current sensor 250. Through this, the present invention solves the second problem.

Since the activated microcontroller 280 has received a request for blood glucose measurement, the microcontroller 280 selects only the blood glucose measurement circuit unit 230 to power on (operation 625). That is, in the present invention, the blood glucose measurement circuit unit 230 is powered on after a request for blood glucose measurement has been received. In addition, as illustrated in FIG. 2 or FIG. 3, this operation is performed through an output pin of the microcontroller 280 connected to the blood glucose measurement circuit unit 230. Accordingly, the present invention solves the above sixth problem corresponding to blood glucose measurement.

Subsequently, the microcontroller 280 starts blood glucose measurement (operation 630). First, between the input terminal of the AD converter 270, connected to the output of the ECG measurement circuit unit 260 and the input terminal of the AD converter 270, connected to the output of the blood glucose measurement circuit unit 230, the microcontroller 280 sets the AD converter 270 to select the latter. This operation is performed by setting a configuration register of the microcontroller 280 related to AD conversion. Subsequently, the microcontroller 280 performs AD conversion in accordance with a predetermined AD conversion period and obtains AD conversion results. In the present invention, the above-described seventh problem corresponding to blood glucose measurement is solved by this operation, firmware for executing this operation, and the circuit of FIG. 2 or FIG. 3.

When the blood glucose measurement is completed, the complex sensor device 170 advertises as a Bluetooth low energy peripheral device (operation 635). Since the advertising operation 635 is performed after the blood glucose measurement is completed, power consumption of the battery 200 embedded in the complex sensor device 170 is reduced. At this time, since the smartphone 410 is in a process of performing scanning as a Bluetooth low energy central device, the smartphone 410 discovers and tries to access the complex sensor device 170. At this time, once the complex sensor device 170 approves the access, the smartphone 410 and the complex sensor device 170 are in a connected state (operation 640). When the complex sensor device 170 is in a connected state, blood glucose measurement data is transmitted to the smartphone 410 (operation 645) and the microcontroller 280 enters into a sleep mode (operation 650).

Although it has been described that for blood glucose measurement, when the blood test strip 178 is inserted into the blood test strip insertion hole 176, the current sensor 220 generates an output, the present invention is not limited thereto. It is possible that the current sensor 220 may detect a minute current and automatically generate an output when a drop of blood is put on the blood test strip 178.

All the circuits of FIGS. 2 and 3 are powered by the battery 200 embedded in the complex sensor device 170. In FIGS. 2 and 3, any mechanical power switch, any mechanical selection switch, and any display are not used. In FIGS. 2 and 3, when the complex sensor device 170 is not in use for measurement, only the blood glucose current sensor 220, the ECG current sensor 250, and the microcontroller 280 consume approximately 1 µA respectively and all the other blocks are completely powered off. That is, total power consumption of the complex sensor device 170 in a waiting mode is approximately 3 µA. The capacity of the commonly used CR2032 is approximately 200 mAh. Thus, a waiting time of the portable complex sensor device 170 using the CR2032 is, for example, about 7.6 years. Much of the power consumed during measurement is consumed for wireless communication and power consumed during measurement is approximately 10 mA. In a case in which ECG measurement is performed for 30 seconds once a day and blood glucose measurement is performed for 5 seconds once a day, based on measurement time including wireless communication, even though power consumed for a waiting period is included, a single CR2032 battery can be used for, for example, about three years.

FIG. 7 illustrates both a flowchart of an application used when an ECG is measured and a flowchart of an application when blood glucose is measured, for the sake of convenience. However, actually, a single measurement flowchart is performed at a time. When a user starts an application according to the present invention, as illustrated in FIG. 4, a variety of touch buttons are displayed on the display 420 of the smartphone 410 (operation 710).

First, the case of ECG measurement will be described. As illustrated in FIG. 7, a flow for ECG measurement consists of two streams: a central stream (operations 722, 724, 726, 728, 730, and 732) and a Bluetooth low energy (BLE) stream (operations 752 and 754). When an application starts, a variety of buttons are displayed on the display 420 of the smartphone 410 (operation 710), and then the BLE stream (operations 752 and 754) for performing Bluetooth low energy communication is started. A user who wants to measure an ECG touches the ECG measurement button 432 (operation 722). Logically, it may be thought that the BLE stream (operations 752 and 754) should start by touching (operation 722) of the ECG measurement button 432. The reason why the BLE stream (operations 752 and 754) starts before the ECG measurement button 432 is touched (operation 722) in the present invention is because operations 772 and 774 in blood glucose measurement may be unnecessary since an intent for blood glucose measurement can be clearly known by insertion of the blood test strip 178 without touching the blood glucose measurement button 442. This is arranged so that the following is accomplished: when the blood glucose measurement strip 178 is inserted, blood glucose measurement is automatically completed, and then blood glucose measurement results are displayed on the display 420 of the smartphone 410.

When a user touches the ECG measurement button 432 (operation 722), a signal for requesting ECG measurement is transmitted to the BLE stream (operations 752 and 754) (operation 724). In addition, a message for requesting a user to touch the pair of electrodes 172 and 174 is displayed on the display 420 of the smartphone 410 (operation 724). In the BLE stream (operations 752 and 754), the signal for requesting ECG measurement is transmitted to the complex sensor device 170.

The complex sensor device 170 having received the signal for requesting ECG measurement performs the ECG measurement operation as illustrated in FIG. 5 and transmits the measured ECG data to the BLE stream (operations 752 and 754). The BLE stream (operations 752 and 754) delivers the ECG data received from the complex sensor device 170 to the central stream (operations 722, 724, 726, 728, 730, and 732). Subsequently, the central stream (operations 722, 724, 726, 728, 730, and 732) receives the ECG data (operation 726). In the central stream (operations 722, 724, 726, 728, 730, and 732), the received ECG data is displayed in a chart form on the display 420 of the smartphone 410 (operation 728). When all the processes for ECG measurement are completed, the measured ECG data is stored in a file form in a smartphone storage device (operation 730). In a state in which the measured ECG data is displayed in a chart form on the display 420 of the smartphone 410, the smartphone application waits for a user to press an application stop button to finish the application (operation 732).

As illustrated in FIG. 7, a flow for blood glucose measurement consists of two streams: a central stream (operations 772, 774, 776, 778, 780, and 782) and a BLE stream (operations 752 and 754). When an application starts, a variety of buttons are displayed on the display 420 of the smartphone 410, and then the BLE stream (operations 752 and 754) for performing Bluetooth low energy communication is started.

When a user touches the blood glucose measurement button 442 (operation 772), a message for requesting a user to insert a blood test strip is displayed on the display 420 of the smartphone 410 (operation 774). However, a signal for requesting blood glucose measurement is not sent to the BLE stream (operations 752 and 754). This is different from a case in which for ECG measurement, when a user presses the ECG measurement button (operation 722), a signal for requesting ECG measurement is sent to the BLE stream (operations 752 and 754) (operation 724). This is because a user does not need to perform operations 772 and 774 to measure blood glucose. This is because, to initiate blood glucose measurement, a user only needs to insert the blood test strip 178 into the blood test strip insertion hole 176.

Operations 772 and 774 are merely arranged based on the assumption that for blood glucose measurement, a user may think he or she should select the blood glucose measurement button of the application and may want to do so. That is, this is because if the blood glucose measurement button 442 is not displayed when a user who wants to measure blood glucose executes the application, the user feels embarrassed with a thought of something is wrong. Thus, in FIG. 7, operation 774 does only displaying a message for requesting a user to insert a blood test strip on the display 420 of the smartphone 410. Accordingly, the above-described fifth problem is solved.

Due to the above-described reason, subsequent operations 776, 778, 780, and 782 are performed even when operations 772 and 774 are not performed by a user. When the blood test strip 178 is inserted into the blood test strip insertion hole 176 (operation 610), the complex sensor device 170 performs the blood glucose measurement described in FIG. 6, and transmits the measured blood glucose data to the BLE stream (operations 752 and 754) (operation 645). The BLE stream (operations 752 and 754) delivers the blood glucose data having received from the complex sensor device 170 to the central stream. Then, the central stream receives the blood glucose data (operation 776). In the central stream, the received blood glucose data is displayed on the display 420 of the smartphone 410 (operation 778).

The above blood glucose measurement method which can be achieved by inserting the blood test strip 178 into the blood test strip insertion hole 176 without performing operations 772 and 774 provides considerable user convenience, simplicity of procedures, and reduced measurement time, compared to the blood glucose measurement method which includes operations 772 and 774. In addition, the present invention which accommodates operations 772 and 774, provides considerable user convenience in that measurement is performed by a user in any manner, and there is no need for a user to thoroughly know usage rules. That is, the present invention accommodates a variety of measurement methods for various users.

After displaying the blood glucose level (operation 778), the measured blood glucose level is stored in a file form in a smartphone storage device (operation 780). In a state in which the measured blood glucose level is displayed on the display 420 of the smartphone 410, a smartphone application waits for a user to press an application termination button and finish blood glucose measurement (operation 782).

As described above, although the present invention has been described for a case in which two pieces of biometric information including an ECG and blood glucose are measured using a single portable complex sensor device and a smartphone application, the present invention is not limited thereto and may be applied to various measurement items and various devices corresponding thereto. According to the present invention, a user can receive desired results without errors for a number of cases of all possible operation orders by using a complex sensor device not including any mechanical switch or mechanical selection switch, and any display, and a smartphone application with increased user convenience.

While the above embodiment discusses a smartphone, one of ordinary skill in the art will appreciate that other devices may be used, and that the invention is not limited to the smartphone. Any kinds of suitable device may be employed. For example, the mobile device may be a smartphone, a smart watch, a tablet such as an iPad, Galaxy tab, a mobile medical device, and/or any portable device which a user uses.

INDUSTRIAL APPLICABILITY

A portable complex sensor device according to the present invention wirelessly communicates with a smartphone and is convenient to carry, thus is not limited by time and place, and may be used as a portable health measurement apparatus for acquiring a plurality of pieces of medical information such as blood glucose, an ECG, and the like.

The invention claimed is:

1. A portable complex sensor device for measuring a plurality of pieces of biometric information, the portable complex sensor device comprising:
    a plurality of biometric information measurement circuit units configured to measure the plurality of pieces of biometric information;
    a plurality of input terminal sets configured to allow each of the plurality of biometric information measurement circuit units to receive an input signal;
    a plurality of current sensors configured such that, when a subject having biometric information is electrically connected to one of the plurality of input terminal sets, a current flows in the subject having biometric information through the electrically connected input terminal set, configured to generate an output signal when sensing the current, and supplied with power at all times;
    an AD converter connected to an output terminal of each of the biometric information measurement circuit units and configured to convert an analog signal into a digital signal;
    a wireless communication device configured to transmit or receive data to or from a mobile device; and
    a microcontroller configured to receive an output of the AD converter,
    wherein the microcontroller is supplied with power of a battery embedded in the portable complex sensor device, when the portable complex sensor device is not in use for biometric information measurement, the microcontroller operates in a sleep mode and the plurality of biometric information measurement circuit units, the AD converter, and the wireless communication device are powered off, the microcontroller operates in an active mode when receiving the output signal of the current sensor, and controls one of the plurality of biometric information measurement circuit units corresponding to the current sensor, the AD converter, and the wireless communication device to be powered on, the portable complex sensor device displays measured biometric information data on a screen of the mobile device, and the portable complex sensor device comprises a plurality of electrocardiogram electrodes and a blood test strip insertion hole at a case of the portable complex sensor device.

2. The portable complex sensor device of claim 1, wherein the plurality of pieces of biometric information comprises electrocardiogram information and blood information.

3. The portable complex sensor device of claim 2, wherein the blood information comprises at least one of a blood glucose level, a ketone level, and an international normalized ratio (INR).

4. The portable complex sensor device of claim 1, wherein the wireless communication device supports Bluetooth low energy (BLE).

5. The portable complex sensor device of claim 1, wherein the current sensed by the current sensor is a direct current.

6. A method of measuring a plurality of pieces of biometric information by using a portable complex sensor device and a mobile device, the method comprising:

displaying a plurality of selection buttons configured to allow a user to select biometric information, on a display of the mobile device when a mobile device application is executed;

when one of the plurality of selection buttons is selected and contacted, transmitting information of the corresponding button to the portable complex sensor device;

activating a microcontroller of the portable complex sensor device using one of a plurality of current sensors;

receiving the information of the corresponding button through a wireless communication device, the receiving being performed by the activated microcontroller;

powering on a biometric information measurement circuit unit corresponding to the received button information and performing a measurement operation, the powering and the performing being performed by the microcontroller;

powering on an AD converter, performing AD conversion of an output of the biometric information measurement circuit unit, and transmitting the output to the microcontroller, the powering being performed by the microcontroller and the performing and transmitting being performed by the AD converter;

transmitting the measured biometric information to the mobile device via the wireless communication device, the transmitting being performed by the microcontroller;

displaying the measured biometric information on a screen of the mobile device; and storing the measured biometric information in a memory of the mobile device.

7. The method of claim 6, wherein the plurality of pieces of biometric information comprises electrocardiogram information and blood information.

8. The method of claim 7, wherein the blood information comprises at least one of a blood glucose level, a ketone level, and an international normalized ratio (INR).

9. The method of claim 8, wherein in a priority order of an interruption for activating the microcontroller, an interruption due to insertion of the blood test strip is prioritized over an interruption due to contact of the electrocardiogram electrodes.

10. The method of claim 7, wherein, when the electrocardiogram information is measured, the method comprises:

bringing a plurality of body sites into contact with a plurality of electrocardiogram electrodes included at a case of the portable complex sensor device;

activating the microcontroller by an electrocardiogram current sensor;

confirming whether an electrocardiogram measurement button is selected in the mobile device via BLE communication;

powering on an electrocardiogram measurement circuit unit; and starting AD conversion for measurement data after confirming again whether the plurality of electrocardiogram electrodes are in a contact state.

11. The method of claim 7, wherein, when the blood information is measured, the method comprises:

inserting a blood test strip into a blood test strip insertion hole included at a case of the portable complex sensor device;

activating the microcontroller by a blood current sensor;
powering on a blood measurement circuit unit; and
performing AD conversion for measurement data.

* * * * *